(12) United States Patent
Cully et al.

(10) Patent No.: US 11,229,512 B2
(45) Date of Patent: Jan. 25, 2022

(54) DIAMETRICALLY ADJUSTABLE ENDOPROSTHESES AND ASSOCIATED SYSTEMS AND METHODS

(71) Applicant: W. L. Gore & Associates, Inc., Newark, DE (US)

(72) Inventors: Edward H. Cully, Flagstaff, AZ (US); Jeffrey B. Duncan, Flagstaff, AZ (US); Marisa L. Sylvester, Flagstaff, AZ (US); Daniel W. Yates, Flagstaff, AZ (US); Michael J. Vonesh, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 388 days.

(21) Appl. No.: 16/094,400

(22) PCT Filed: Apr. 21, 2016

(86) PCT No.: PCT/US2016/028671
§ 371 (c)(1),
(2) Date: Oct. 17, 2018

(87) PCT Pub. No.: WO2017/184153
PCT Pub. Date: Oct. 26, 2017

(65) Prior Publication Data
US 2019/0125517 A1    May 2, 2019

(51) Int. Cl.
*A61F 2/07* (2013.01)
*A61F 2/958* (2013.01)
(Continued)

(52) U.S. Cl.
CPC .............. *A61F 2/07* (2013.01); *A61F 2/958* (2013.01); *A61M 27/002* (2013.01);
(Continued)

(58) Field of Classification Search
CPC ........ A61F 2002/072; A61F 2002/9583; A61F 2230/001; A61F 2250/001;
(Continued)

(56) References Cited

U.S. PATENT DOCUMENTS 3,953,566 A   4/1976  Gore
4,187,390 A   2/1980  Gore
(Continued)

FOREIGN PATENT DOCUMENTS

CA       2462509 A1    4/2003
CN     101420913 A     4/2009
(Continued)

OTHER PUBLICATIONS

European Search Report and Search Opinion Received for EP Application No. 16899644.5, dated Oct. 30, 2019, 8 pages.
(Continued)

*Primary Examiner* — Brooke Nicole Labranche

(57) ABSTRACT

A diametrically adjustable endoprosthesis includes a controlled expansion element extending along at least a portion of a graft and is supported by a stent. The controlled expansion element diametrically constrains and limits expansion of the endoprosthesis. Upon deployment from a smaller, delivery configuration, the endoprosthesis can expand to the initial diameter set by the controlled expansion element. Thereafter, the endoprosthesis can be further diametrically expanded (e.g., using balloon dilation) by mechanically altering the controlled expansion element.

9 Claims, 5 Drawing Sheets

(51) Int. Cl.
   *A61M 27/00* (2006.01)
   *A61M 1/36* (2006.01)
   *A61M 25/10* (2013.01)

(52) U.S. Cl.
   CPC . *A61F 2002/072* (2013.01); *A61F 2002/9583* (2013.01); *A61F 2250/001* (2013.01); *A61F 2250/0039* (2013.01); *A61F 2250/0048* (2013.01); *A61F 2250/0098* (2013.01); *A61M 1/3655* (2013.01); *A61M 2025/1004* (2013.01); *A61M 2210/1071* (2013.01)

(58) Field of Classification Search
   CPC ...... A61F 2250/0039; A61F 2250/0048; A61F 2250/0098; A61F 2/07; A61F 2/958; A61M 1/3655; A61M 2025/1004; A61M 2210/1071; A61M 27/002
   See application file for complete search history.

(56) References Cited

U.S. PATENT DOCUMENTS

| | | | |
|---|---|---|---|
| 4,332,035 A | 6/1982 | Mano | |
| 4,877,661 A | 10/1989 | House et al. | |
| 4,955,899 A | 9/1990 | Della et al. | |
| 5,026,513 A | 6/1991 | House et al. | |
| 5,064,435 A | 11/1991 | Porter | |
| 5,071,609 A | 12/1991 | Tu et al. | |
| 5,476,589 A | 12/1995 | Bacino | |
| 5,534,007 A | 7/1996 | St et al. | |
| 5,549,663 A | 8/1996 | Cottone, Jr. | |
| 5,673,102 A | 9/1997 | Suzuki et al. | |
| 5,708,044 A | 1/1998 | Branca | |
| 5,718,973 A | 2/1998 | Lewis et al. | |
| 5,749,852 A | 5/1998 | Schwab et al. | |
| 5,752,934 A | 5/1998 | Campbell et al. | |
| 5,759,192 A | 6/1998 | Saunders | |
| 5,769,884 A | 6/1998 | Solovay | |
| 5,772,884 A | 6/1998 | Tanaka et al. | |
| 5,788,626 A | 8/1998 | Thompson | |
| 5,814,405 A | 9/1998 | Branca et al. | |
| 5,824,043 A | 10/1998 | Cottone, Jr. | |
| 5,843,158 A | 12/1998 | Lenker et al. | |
| 5,843,161 A | 12/1998 | Solovay | |
| 5,843,171 A | 12/1998 | Campbell et al. | |
| 5,853,419 A | 12/1998 | Imran | |
| 5,925,061 A | 7/1999 | Ogi et al. | |
| 5,935,162 A | 8/1999 | Dang | |
| 5,957,974 A | 9/1999 | Thompson et al. | |
| 6,010,529 A | 1/2000 | Herweck et al. | |
| 6,013,854 A | 1/2000 | Moriuchi | |
| 6,042,588 A | 3/2000 | Munsinger et al. | |
| 6,042,605 A | 3/2000 | Martin et al. | |
| 6,042,606 A | 3/2000 | Frantzen | |
| 6,110,198 A | 8/2000 | Fogarty et al. | |
| 6,156,064 A * | 12/2000 | Chouinard | A61F 2/07 623/1.44 |
| 6,161,399 A | 12/2000 | Jayaraman | |
| 6,165,211 A | 12/2000 | Thompson | |
| 6,174,329 B1 | 1/2001 | Callol et al. | |
| 6,190,406 B1 | 2/2001 | Duerig et al. | |
| 6,217,609 B1 | 4/2001 | Haverkost | |
| 6,245,012 B1 | 6/2001 | Kleshinski | |
| 6,261,320 B1 | 7/2001 | Tam et al. | |
| 6,261,620 B1 | 7/2001 | Leadbeater | |
| 6,315,791 B1 | 11/2001 | Gingras et al. | |
| 6,336,937 B1 | 1/2002 | Vonesh et al. | |
| 6,352,552 B1 | 3/2002 | Levinson et al. | |
| 6,379,382 B1 | 4/2002 | Yang | |
| 6,436,132 B1 | 8/2002 | Patel et al. | |
| 6,461,665 B1 | 10/2002 | Scholander | |
| 6,488,701 B1 | 12/2002 | Nolting et al. | |
| 6,541,589 B1 | 4/2003 | Baillie | |
| 6,620,190 B1 | 9/2003 | Colone | |
| 6,626,939 B1 | 9/2003 | Burnside et al. | |
| 6,673,102 B1 | 1/2004 | Vonesh et al. | |
| 6,673,107 B1 | 1/2004 | Brandt et al. | |
| 6,730,120 B2 | 5/2004 | Berg et al. | |
| 6,755,856 B2 | 6/2004 | Fierens et al. | |
| 6,758,858 B2 | 7/2004 | McCrea et al. | |
| 6,890,350 B1 | 5/2005 | Walak | |
| 7,022,132 B2 | 4/2006 | Kocur | |
| 7,049,380 B1 | 5/2006 | Chang et al. | |
| 7,083,642 B2 | 8/2006 | Sirhan et al. | |
| 7,105,018 B1 | 9/2006 | Yip et al. | |
| 7,306,729 B2 | 12/2007 | Bacino et al. | |
| 7,419,678 B2 | 9/2008 | Falotico | |
| 7,462,675 B2 | 12/2008 | Chang et al. | |
| 7,531,611 B2 | 5/2009 | Sabol et al. | |
| 7,704,274 B2 | 4/2010 | Boyle et al. | |
| 7,789,908 B2 | 9/2010 | Sowinski et al. | |
| 7,811,314 B2 | 10/2010 | Fierens et al. | |
| 7,815,763 B2 | 10/2010 | Fierens et al. | |
| 7,887,562 B2 | 2/2011 | Young et al. | |
| 7,927,364 B2 | 4/2011 | Fierens et al. | |
| 7,927,365 B2 | 4/2011 | Fierens et al. | |
| 7,935,141 B2 | 5/2011 | Randall et al. | |
| 7,967,829 B2 | 6/2011 | Gunderson et al. | |
| 8,048,440 B2 | 11/2011 | Chang et al. | |
| 8,545,525 B2 | 10/2013 | Surti et al. | |
| 8,585,753 B2 | 11/2013 | Scanlon et al. | |
| 8,728,103 B2 | 5/2014 | Surti et al. | |
| 8,801,774 B2 | 8/2014 | Silverman | |
| 8,936,634 B2 | 1/2015 | Irwin et al. | |
| 9,241,695 B2 | 1/2016 | Peavey et al. | |
| 9,345,601 B2 | 5/2016 | Jantzen et al. | |
| 9,399,085 B2 | 7/2016 | Cleek et al. | |
| 9,554,786 B2 | 1/2017 | Carley et al. | |
| 9,681,948 B2 | 6/2017 | Levi et al. | |
| 9,737,422 B2 | 8/2017 | Armstrong et al. | |
| 9,795,496 B2 | 10/2017 | Armstrong et al. | |
| 9,839,540 B2 | 12/2017 | Armstrong et al. | |
| 9,931,193 B2 | 4/2018 | Cully et al. | |
| 10,166,128 B2 | 1/2019 | Armstrong et al. | |
| 10,279,084 B2 | 5/2019 | Goepfrich et al. | |
| 10,335,298 B2 | 7/2019 | Armstrong et al. | |
| 10,507,124 B2 | 12/2019 | Armstrong et al. | |
| 2001/0053929 A1 | 12/2001 | Vonesh et al. | |
| 2002/0038140 A1 | 3/2002 | Yang et al. | |
| 2002/0076542 A1 | 6/2002 | Kramer et al. | |
| 2002/0161388 A1 | 10/2002 | Samuels et al. | |
| 2002/0198588 A1 | 12/2002 | Armstrong et al. | |
| 2003/0055494 A1 | 3/2003 | Bezuidenhout et al. | |
| 2003/0060871 A1 | 3/2003 | Hill et al. | |
| 2003/0180488 A1 | 9/2003 | Lim et al. | |
| 2004/0024442 A1 | 2/2004 | Sowinski et al. | |
| 2004/0024448 A1 | 2/2004 | Chang et al. | |
| 2004/0044400 A1 | 3/2004 | Cheng et al. | |
| 2004/0044401 A1 | 3/2004 | Bales et al. | |
| 2004/0133266 A1 | 7/2004 | Clerc et al. | |
| 2004/0162606 A1 | 8/2004 | Thompson | |
| 2004/0170782 A1 | 9/2004 | Wang et al. | |
| 2004/0224442 A1 | 11/2004 | Grigg | |
| 2004/0260277 A1 | 12/2004 | Maguire | |
| 2005/0080476 A1 | 4/2005 | Gunderson et al. | |
| 2005/0137680 A1 | 6/2005 | Ortiz et al. | |
| 2005/0273149 A1 | 12/2005 | Tran et al. | |
| 2005/0283224 A1 | 12/2005 | King | |
| 2006/0009835 A1 | 1/2006 | Osborne et al. | |
| 2006/0015171 A1 | 1/2006 | Armstrong | |
| 2006/0036311 A1 | 2/2006 | Nakayama et al. | |
| 2006/0106337 A1 | 5/2006 | Blankenship | |
| 2006/0118236 A1 | 6/2006 | House et al. | |
| 2006/0135985 A1 | 6/2006 | Cox et al. | |
| 2006/0161241 A1 | 7/2006 | Barbut et al. | |
| 2006/0190070 A1 | 8/2006 | Dieck et al. | |
| 2006/0259133 A1 | 11/2006 | Sowinski et al. | |
| 2006/0271091 A1 | 11/2006 | Campbell et al. | |
| 2006/0276883 A1 | 12/2006 | Greenberg et al. | |
| 2007/0012624 A1 | 1/2007 | Bacino et al. | |
| 2007/0060999 A1 | 3/2007 | Randall et al. | |
| 2007/0088421 A1 | 4/2007 | Loewen | |
| 2007/0129786 A1 | 6/2007 | Beach et al. | |
| 2007/0207186 A1 | 9/2007 | Scanlon et al. | |

(56) References Cited

U.S. PATENT DOCUMENTS

| | | |
|---|---|---|
| 2007/0207816 A1 | 9/2007 | Spain, Jr. |
| 2007/0208421 A1 | 9/2007 | Quigley |
| 2007/0213800 A1 | 9/2007 | Fierens et al. |
| 2007/0250146 A1 | 10/2007 | Cully et al. |
| 2007/0250153 A1 | 10/2007 | Cully et al. |
| 2007/0254012 A1 | 11/2007 | Ludwig et al. |
| 2008/0051876 A1 | 2/2008 | Ta et al. |
| 2008/0097301 A1 | 4/2008 | Alpini et al. |
| 2008/0097401 A1 | 4/2008 | Trapp et al. |
| 2008/0097579 A1 | 4/2008 | Shanley et al. |
| 2008/0097582 A1 | 4/2008 | Shanley et al. |
| 2008/0119943 A1 | 5/2008 | Armstrong et al. |
| 2008/0319531 A1 | 12/2008 | Doran et al. |
| 2009/0005854 A1 | 1/2009 | Huang et al. |
| 2009/0030499 A1 | 1/2009 | Bebb et al. |
| 2009/0036976 A1 | 2/2009 | Beach et al. |
| 2009/0043373 A1 | 2/2009 | Arnault et al. |
| 2009/0104247 A1 | 4/2009 | Pacetti |
| 2009/0182413 A1 | 7/2009 | Burkart et al. |
| 2009/0306762 A1 | 12/2009 | McCullagh et al. |
| 2009/0306766 A1 | 12/2009 | McDermott et al. |
| 2010/0016940 A1 | 1/2010 | Shokoohi et al. |
| 2010/0094394 A1 | 4/2010 | Beach et al. |
| 2010/0094405 A1 | 4/2010 | Cottone |
| 2010/0106240 A1 | 4/2010 | Duggal et al. |
| 2010/0159171 A1 | 6/2010 | Clough |
| 2010/0256738 A1 | 10/2010 | Berglund |
| 2010/0286760 A1 | 11/2010 | Beach et al. |
| 2010/0305682 A1 | 12/2010 | Furst |
| 2011/0009953 A1 | 1/2011 | Luk et al. |
| 2011/0087318 A1 | 4/2011 | Daugherty et al. |
| 2012/0323211 A1 | 12/2012 | Ogle et al. |
| 2013/0131780 A1 | 5/2013 | Armstrong et al. |
| 2013/0183515 A1 | 7/2013 | White |
| 2013/0184807 A1 | 7/2013 | Kovach et al. |
| 2013/0197624 A1 | 8/2013 | Armstrong et al. |
| 2013/0204347 A1 | 8/2013 | Armstrong et al. |
| 2013/0253466 A1 | 9/2013 | Campbell et al. |
| 2013/0297003 A1 | 11/2013 | Pinchuk |
| 2014/0135897 A1 | 5/2014 | Cully et al. |
| 2014/0172066 A1 | 6/2014 | Goepfrich et al. |
| 2014/0180402 A1 | 6/2014 | Bruchman et al. |
| 2015/0005870 A1 | 1/2015 | Kovach et al. |
| 2015/0157770 A1 | 6/2015 | Cully et al. |
| 2015/0313871 A1 | 11/2015 | Li et al. |
| 2016/0015422 A1 | 1/2016 | De et al. |
| 2016/0184079 A1* | 6/2016 | Scutti ........................ A61F 2/07 623/1.13 |
| 2017/0065400 A1 | 3/2017 | Armstrong et al. |
| 2017/0105854 A1 | 4/2017 | Treacy et al. |
| 2017/0106176 A1 | 4/2017 | Taft et al. |
| 2017/0216062 A1 | 8/2017 | Armstrong et al. |
| 2018/0177583 A1 | 6/2018 | Cully et al. |
| 2019/0209739 A1 | 7/2019 | Goepfrich et al. |
| 2019/0216592 A1 | 7/2019 | Cully et al. |
| 2020/0179663 A1 | 6/2020 | McDaniel et al. |
| 2020/0237497 A1 | 7/2020 | Silverman et al. |
| 2021/0038413 A1 | 2/2021 | Cully et al. |
| 2021/0068996 A1 | 3/2021 | Armstrong et al. |

FOREIGN PATENT DOCUMENTS

| | | |
|---|---|---|
| CN | 101926699 A | 12/2010 |
| CN | 201744060 U | 2/2011 |
| CN | 102015009 A | 4/2011 |
| CN | 103945796 A | 7/2014 |
| EP | 0293090 A2 | 11/1988 |
| EP | 0313263 A2 | 4/1989 |
| EP | 0582870 A2 | 2/1994 |
| EP | 0775472 A2 | 5/1997 |
| EP | 0815806 A2 | 1/1998 |
| EP | 0893108 A2 | 1/1999 |
| EP | 1666003 A1 | 6/2006 |
| EP | 2255750 A2 | 12/2010 |
| JP | 02-000645 A | 1/1990 |
| JP | 09-241412 A | 9/1997 |
| JP | 11-290448 A | 10/1999 |
| JP | 11-512635 A | 11/1999 |
| JP | 2001-509702 A | 7/2001 |
| JP | 2007-526098 A | 9/2007 |
| JP | 2008-506459 A | 3/2008 |
| JP | 2010-500107 A | 1/2010 |
| JP | 2010-504174 A | 2/2010 |
| JP | 2010-535075 A | 11/2010 |
| JP | 2018-134425 A | 8/2018 |
| JP | 2021-122433 A | 8/2021 |
| RU | 2124986 C1 | 1/1999 |
| WO | 94/13224 A1 | 6/1994 |
| WO | 94/16802 A1 | 8/1994 |
| WO | 95/05555 A1 | 2/1995 |
| WO | 95/09586 A1 | 4/1995 |
| WO | 96/07370 A1 | 3/1996 |
| WO | 96/40348 A1 | 12/1996 |
| WO | 97/10871 A1 | 3/1997 |
| WO | 99/26558 A1 | 6/1999 |
| WO | 00/41649 A1 | 7/2000 |
| WO | 00/47271 A1 | 8/2000 |
| WO | 01/64278 A1 | 9/2001 |
| WO | 01/74272 A2 | 10/2001 |
| WO | 02/60506 A1 | 8/2002 |
| WO | 03/03946 A1 | 1/2003 |
| WO | 03/20175 A1 | 3/2003 |
| WO | 2004/000375 A1 | 12/2003 |
| WO | 2006/019626 A2 | 2/2006 |
| WO | 2006/058322 A2 | 6/2006 |
| WO | 2008/021002 A1 | 2/2008 |
| WO | 2008/028964 A2 | 3/2008 |
| WO | 2008/036870 A2 | 3/2008 |
| WO | 2008/049045 A2 | 4/2008 |
| WO | 2008/021006 A3 | 8/2008 |
| WO | 2008/097589 A1 | 8/2008 |
| WO | 2009/017827 A1 | 2/2009 |
| WO | 2009/100210 A1 | 8/2009 |
| WO | 2009/108355 A1 | 9/2009 |
| WO | 2010/006783 A1 | 1/2010 |
| WO | 2010/008570 A1 | 1/2010 |
| WO | 2010/030766 A1 | 3/2010 |
| WO | 2010/132707 A1 | 11/2010 |
| WO | 2010/150208 A2 | 12/2010 |
| WO | 2011/098565 A1 | 8/2011 |
| WO | 2012/011261 A1 | 1/2012 |
| WO | 2012/099979 A1 | 7/2012 |
| WO | 2012/158944 A1 | 11/2012 |
| WO | 2013/074663 A2 | 5/2013 |
| WO | 2013/074990 A1 | 5/2013 |
| WO | 2013/109337 A1 | 7/2013 |
| WO | 2017/038145 A1 | 3/2017 |
| WO | 2019/074869 A1 | 4/2019 |

OTHER PUBLICATIONS

European Search Report and Search Opinion Received for EP Application No. 18167101, dated Jul. 25, 2018, 9 pages.
European Search Report from EP16196687.4, dated Nov. 21, 2017, 5 pages.
Extended European Search Report issued in EP Application No. 17186750.0, dated Oct. 24, 2017, 7 pages.
International Preliminary Report on Patentability issued in PCT/US2016/028671, dated Nov. 1, 2018, 12 pages.
International Preliminary Report on Patentability received for PCT Patent Application No. PCT/US11/61165, dated Jul. 25, 2013, 14 pages.
International Preliminary Report on Patentability received for PCT Patent Application No. PCT/US12/65066, dated May 30, 2014, 14 pages.
International Preliminary Report on Patentability received for PCT Patent Application No. PCT/US14/68430, dated Jun. 16, 2016, 8 pages.
International Preliminary Report on Patentability received for PCT Patent Application No. PCT/US2013/076405, dated Jul. 2, 2015, 10 pages.

(56) References Cited

OTHER PUBLICATIONS

International Preliminary Report on Patentability received for PCT Patent Application No. PCT/US2014/013496, dated Aug. 11, 2016, 7 pages.
International Search Report and Written Opinion for Application No. PCT/US2016/028671, dated Jul. 28, 2016, 19 pages.
International Search Report and Written Opinion for PCT/US2012/064908 dated Feb. 4, 2013, corresponding to U.S. Appl. No. 13/675,730, 11 pages.
International Search Report and Written Opinion for PCT/US2012/066518, dated Feb. 4, 2013, corresponding to U.S. Appl. No. 13/351,052, 12 pages.
International Search Report and Written Opinion for PCT/US2014/068430 dated Feb. 20, 2015, corresponding to U.S. Appl. No. 14/558,296, 9 pages.
International Search Report and Written Opinion issued in PCT/US2011/061165, dated Oct. 1, 2012, 20 pages.
International Search Report and Written Opinion issued in PCT/US2012/064908, dated Feb. 4, 2013, 10 pages.
International Search Report and Written Opinion issued in PCT/US2012065066, dated Nov. 11, 2013, 9 pages.
International Search Report and Written Opinion issued in PCT/US2016/028671, dated Jul. 28, 2016, 19 pages.
International Search Report for PCT/US2013/076405 dated May 6, 2014, corresponding to U.S. Appl. No. 14/132,767, 8 pages.
International Search Report for PCT/US2014/013496 dated Dec. 2, 2014, corresponding to U.S. Appl. No. 13/755,481, 4 pages.
International Search Report issued in PCT/US2013/076405, dated May 6, 2014, 7 pages.
International Search Report issued in PCT/US2014/013496, dated Dec. 2, 2014, 3 pages.
International Written Opinion received for PCT Patent Application No. PCT/US2014/013496, dated Dec. 2, 2014, 5 pages.
Nakayama, Yasuhide. Microporous Stent Achieves Brain Aneurysm Occlusion Without Disturbing Branching Flow. NeuroNews Nov. 2012; 8:1-2.
Nishi S, Nakayama Y, Ishibashi-Ueda H, Okamoto Y, Yoshida M. Development of microporous self-expanding stent grafts for treating cerebral aneurysms: designing micropores to control intimal hyperplasia. J Artif Organs 2011; 14:348-356.
Partial International Search Report for PCT/US2012/065066, dated Jul. 1, 2013, corresponding to U.S. Appl. No. 13/675,959, 3 pages.

\* cited by examiner

DIAMETRICALLY ADJUSTABLE ENDOPROSTHESES AND ASSOCIATED SYSTEMS AND METHODS

CROSS-REFERENCE TO RELATED APPLICATION

This application is a U.S. 371 Application of International Application PCT/US2016/028671, filed Apr. 21, 2016, which is herein incorporated by reference in its entirety.

BACKGROUND

Various bodily lumens, including those of the body's various circulatory systems, are sensitive to internal fluid pressures. For example, it is known that diseased or damaged liver tissue may increase the resistance to hepatic perfusion resulting in excessive and often dangerous fluid pressure increases in the portal vascular circulation. This condition can lead to gastrointestinal variceal hemorrhage and pathological conditions such as ascites.

In order to decompress the portal circulation, a transjugular intrahepatic portosystemic shunt (TIPS) may be created through the liver tissue by connecting the portal vein to the inferior vena cava via the hepatic vein. This procedure includes forming a pathway directly through the liver to allow direct flow between the portal vein and the hepatic vein. In some treatment methods, the pathway is maintained and lined with a stent or stent-graft to form a shunt. The TIPS procedure has proven to be safe and effective at decompressing the portal system and in controlling acute variceal hemorrhage, for example.

U.S. Pat. No. 6,673,102 to Vonesh et al. describes endovascular devices for use in transjugular intrahepatic portosystemic shunt (TIPS) procedures, including devices that employ a two-part stent-graft construction that provides a low permeability membrane to line the shunt and an uncovered stent portion designed to reside in the portal vein. The devices provide numerous features, including having a compact delivery profile, being easy to accurately deploy, and incorporation of resistance to tissue and bile ingress.

SUMMARY

This disclosure provides diametrically adjustable endoprosthesis designs and associated systems and methods that incorporate various advantages, including the ability to adjust endoprosthesis diameter, and thus achieve desirable fluid flow and fluid pressures across the endoprostheses. In various implementations, the endoprostheses include controlled expansion elements coupled to grafts or stent-grafts. In some designs including self-expanding stent-grafts, one or more controlled expansion elements diametrically constrain and limit expansion of the self-expanding stent-grafts following initial deployment. The stent-grafts self-expand to an initial diameter and can be mechanically altered over a range of diameters due to the constraining elements being able to maintain the adjusted diameter under physiologic conditions. Following initial deployment, the stent-grafts are capable of being further diametrically expanded, for example using balloon dilation. In various implementations, these subsequent, diametric adjustments are achieved by mechanically altering (e.g., plastically deforming) the controlled expansion elements beyond the initial diameters set by the controlled expansion elements. Once altered, the controlled expansion elements are configured to reliably maintain the adjusted diameter at physiologic conditions. In some designs, the stent-grafts have maximum diametric expansion limits (e.g., the as manufactured diameters) that define the upper ends of the ranges to which the endoprostheses can be adjusted, such that diametric adjustments can be made from the initial diameter up to the maximum designed stent-graft diameter.

Some embodiments relate to a diametrically adjustable endoprosthesis including a stent-graft and a controlled expansion element. The stent-graft includes a stent and a base graft secured to the stent. The base graft has a first end and a second end and the stent-graft is self-expanding and exhibits a self-expansion force. The stent-graft has a maximum diametric expansion limit. The controlled expansion element has a continuous wall and an initial diametric expansion limit. The controlled expansion element is adjustable to an adjusted diameter in a range of diameters between the initial diametric expansion limit and the maximum diametric expansion limit when placed under an expansion force in addition to that of the self-expansion force of the stent-graft. The controlled expansion element is configured to maintain the adjusted diameter under physiological conditions following removal of the expansion force and the stent-graft is configured to limit the range of diameters for the adjusted diameter to the maximum diametric expansion limit.

In some methods of treatment, following initial deployment and seating of an endoprosthesis, a user (e.g., clinician) obtains one or more fluid pressure measurements from the circulatory system into which the endoprosthesis is placed. The user is then able to adjust system pressure by adjusting the diameter of the endoprosthesis, the endoprosthesis being configured to maintain the adjusted-to diameter. Such measurements and adjustments may occur at the time of initial implantation, or as part of another procedure performed hours, days, weeks, or even years later. In some methods of treatment, the user can predetermine (e.g., prior to initial implantation) that a diametric adjustment will be desired and make the desired diametric adjustment at the time of implantation.

Some examples of treatments benefiting from this adjustability feature include intrahepatic portosystemic shunts. Intrahepatic portosystemic shunts are commonly performed endoluminally through the jugular vein, connecting the portal vein to the inferior vena cava by way of the hepatic vein. Such a procedure is commonly referred to as being a "transjugular intrahepatic portosystemic shunt" or abbreviated "TIPS" or "TIPSS." It should be appreciated, however, that a shunt through the liver between the portal vein and the vena cava may be accomplished by other methods. As such, the term "intrahepatic portosystemic shunt" as used herein is intended to include any procedure whereby pressure is relieved in the portal vein by way of a shunt from the portal to the systemic systems. Additionally, the instant disclosure describes various advantages of endoprosthesis designs and associated treatment methods for forming intrahepatic portosystemic shunts by way of example, although it should be appreciated the various concepts are also applicable to other types of treatments, such as providing diametrical reserve for treatment of endoleaks, gall bladder drainage, pediatric shunts, fistulas, AV access, for sealing of side branch devices, and for allowance for future lumen narrowing and adjustability to custom fit to tapered anatomy, among others.

Some embodiments relate to a method of forming an intrahepatic portosystemic shunt. The method includes positioning an endoprosthesis in a liver of a patient at a delivery diametrical dimension, the endoprosthesis comprising a self-expanding stent-graft and a controlled expansion element. The endoprosthesis is deployed such that the endoprosthesis self-expands and is seated in the liver of the patient to form an intrahepatic portosystemic shunt, the controlled expansion element limiting expansion of a diametrically controlled portion of the endoprosthesis to an initial deployed diametrical dimension such that the initial deployed diametrical dimension is maintained under physiologic conditions. An internal pressure is applied to the endoprosthesis after deploying the endoprosthesis such that at least a portion of the controlled expansion element is mechanically altered and the diametrical dimension of the diametrically controlled portion of the endoprosthesis is selectively enlarged to an enlarged diametrical dimension and maintained at the enlarged diametrical dimension under physiologic conditions.

Some embodiments relate to a method for treating portal hypertension. The method includes providing an endoprosthesis including a stent, a first graft portion, and a second graft portion extending along at least a portion of the first graft portion, the endoprosthesis being constrained to a first diametrical dimension by a delivery constraint for insertion into a lumen and configured to self-expand to a second enlarged diametrical dimension when the delivery constraint is released, the second graft portion defining a diametrically controlled portion of the endoprosthesis that is restricted from further diametrical enlargement by self-expansion to a restricted diameter. The endoprosthesis is positioned in the portal vein and the hepatic vein. The endoprosthesis is deployed to the second enlarged diametrical dimension by releasing the delivery constraint and allowing the endoprosthesis to self-expand, the diametrically controlled portion maintaining the restricted diameter under physiologic conditions. A diametric adjustment of the endoprosthesis is performed in situ, including diametrically expanding at least a portion of the diametrically controlled portion of the endoprosthesis to an adjusted diameter by applying distending force to the diametrically controlled portion of the endoprosthesis, the diametrically controlled portion of the endoprosthesis maintaining the adjusted diameter under physiologic conditions.

Some embodiments relate to a method for treating portal hypertension including taking at least one pressure measurement to determine a pressure gradient resulting from a shunt formed by an endoprosthesis between the portal vein and the systemic venous circulation at least 24 hours after formation of the shunt. The endoprosthesis includes a self-expanding stent having at least a first segment and a second segment, a graft component on the first segment, at least a portion of the graft component being maintained at an initial deployment diameter by a controlled expansion element that is mechanically adjustable, and diametrically expanding the controlled expansion element by mechanically adjusting the controlled expansion element with a distensive force such that at least a portion of the graft component being maintained at the initial deployment diameter by the controlled expansion element is enlarged and maintained at an enlarged diameter by the controlled expansion element to reduce the pressure gradient.

Some embodiments relate to methods of making endoprostheses. Some embodiments include securing a stent to a base graft to form a stent-graft, positioning a controlled expansion element along the stent-graft, and coupling the controlled expansion element to the stent-graft. The controlled expansion element can be an intermediate layer within the graft portion, an outermost layer outside of the graft portion, or an innermost layer inside of the graft portion. Additionally, multiple controlled expansion elements at any of the foregoing positions are contemplated. The controlled expansion element can be incorporated into at least a portion of the graft portion or underlay or overlay at least a portion of the graft portion of the endoprosthesis. The controlled expansion element can be coupled to the stent-graft by adhesive or mechanical fit for example, or by incorporating the controlled expansion element into the graft portion.

In some embodiments, the stent-graft and controlled expansion portion are coupled by mechanically adjusting the controlled expansion element from a first diameter to the initial diametric expansion limit, the first diameter being smaller than the initial diametric expansion limit. Some additional aspects of methods of making diametrically adjustable endoprostheses according to the instant disclosure include securing a stent that is self-expanding to a base graft to form a stent-graft, positioning a controlled expansion element having a continuous wall about a portion of the stent-graft, and coupling the controlled expansion element to the stent-graft. In some embodiments, coupling the controlled expansion element to the stent-graft includes mechanically adjusting the controlled expansion element to an initial diametric expansion limit corresponding to a diameter to which the endoprosthesis self-expands in an unconstrained state.

In some instances, the base graft includes expanded PTFE having a crystalline melt temperature, and further wherein the controlled expansion element is coupled to the stent-graft component at a temperature that is less than the crystalline melt temperature. Also, the controlled expansion element is optionally coupled to the stent-graft components such that the controlled expansion element is able to change in longitudinal dimension (e.g., longitudinally contract during radial expansion) at a different rate than the stent-graft at a sliding interface. For example, one or more portions of the interface between the stent-graft and controlled expansion element are not bonded or otherwise attached in a manner that would prevent differential longitudinal contraction during expansion of the endoprosthesis.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1:
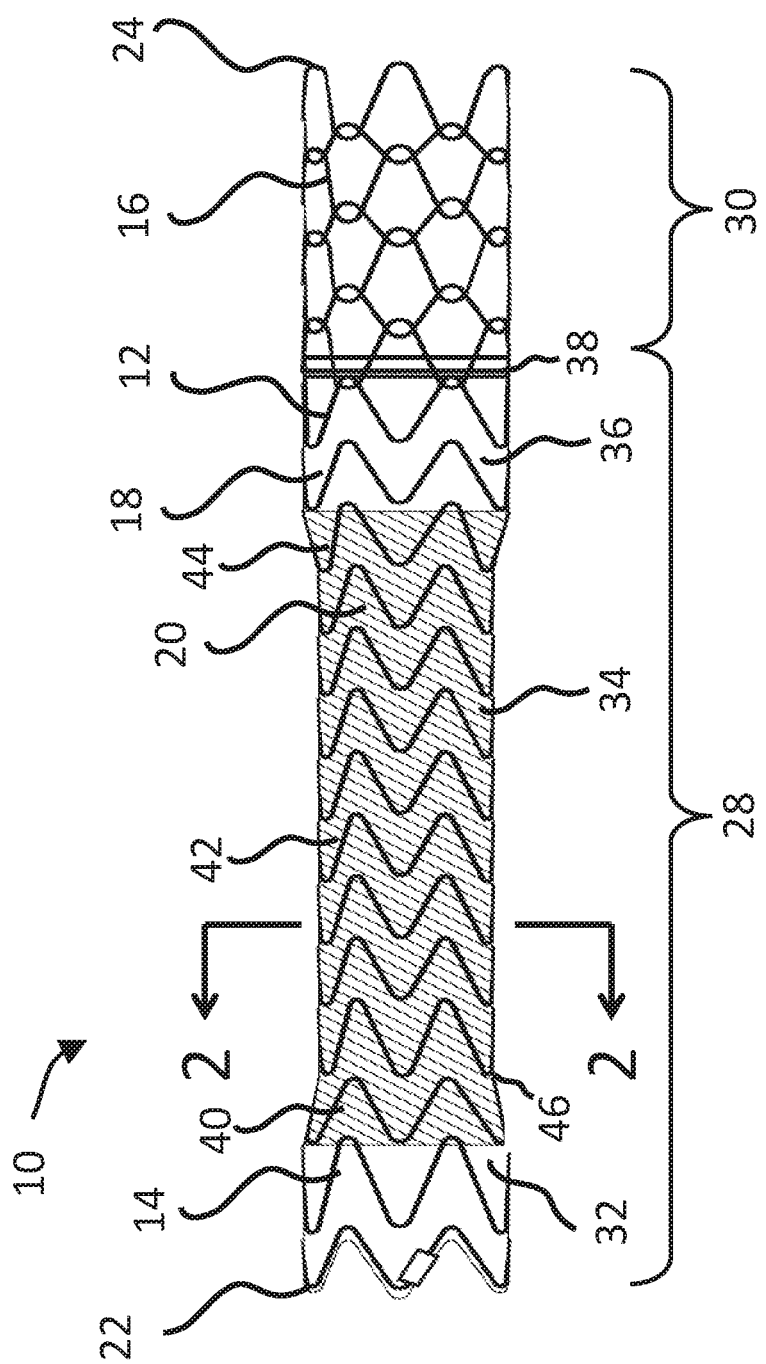
FIG. 1 shows a diametrically adjustable endoprosthesis, according to some embodiments.
Figure 2:
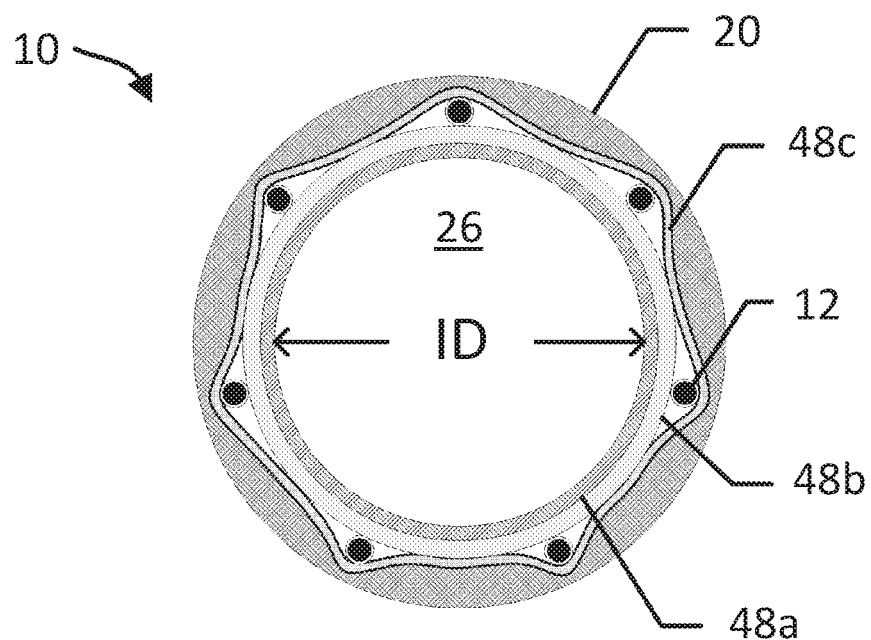
FIG. 2 shows a cross-sectional view of the endoprosthesis of FIG. 1 taken along line 2-2 in FIG. 1, according to some embodiments.
Figure 3:
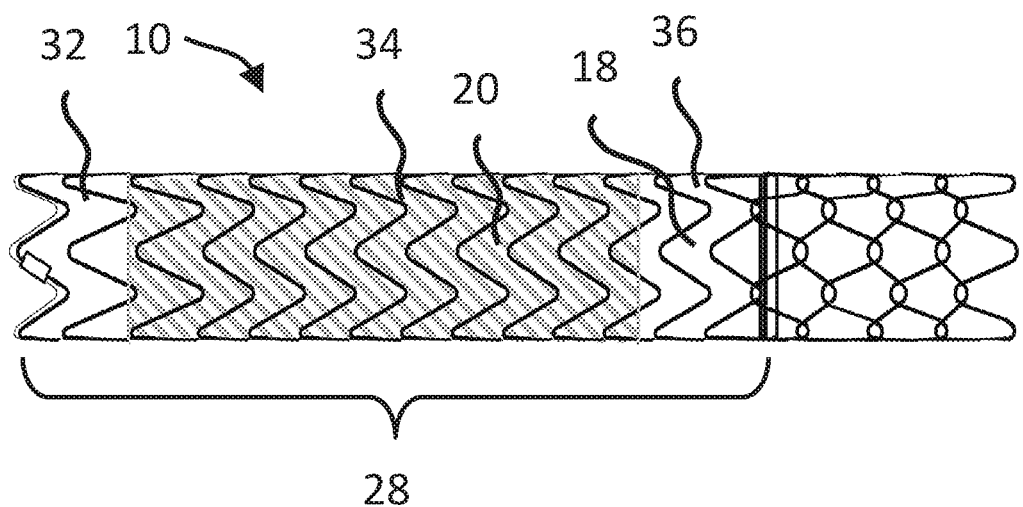
FIG. 3 shows the endoprosthesis of FIG. 1 at an adjusted diameter, according to some embodiments.

FIG. 1 shows a diametrically adjustable endoprosthesis 10, according to some embodiments. As shown, the endoprosthesis 10 includes a stent 12, also described as a stent element or support. The stent 12 has a first segment 14 and a second segment 16. As shown, a base graft 18, also described as a first graft portion, a cover or a liner, is provided along the length of the first segment 14, while a portion of the second segment 16 extends beyond the base graft 18 and is left largely uncovered. The terms "graft," "cover," and "liner" are used interchangeably herein, and are not meant to require a certain relative position with respect to the stent 12. A "liner" may surround the stent 12, a "cover" may be received entirely within the stent 12, and a "lined region" corresponds to a portion of an endoprosthesis including a graft layer, regardless of whether the graft resides inside, outside, sandwiches, or is otherwise positioned relative to a stent element. The endoprosthesis 10 also includes a controlled expansion element 20, also described as a second graft portion. In FIGS. 1 and 3, the controlled expansion element 20 is called out with cross-hatching in FIGS. 1 and 3 for ease of visualization. The controlled expansion element 20 extends along at least a portion of the base graft 18 and optionally enhances or augments one or more functions of the base graft 18, for example serving as a functional graft component of the base graft 18. As shown, the endoprosthesis 10 has a proximal end 22 and a distal end 24 and defines an inner lumen 26 (FIG. 2). In order to facilitate placement of the endoprosthesis 10, radiopaque markers are provided along the length of the endoprosthesis 10 as desired.

As shown in FIG. 1, the assembled endoprosthesis 10 includes a graft-lined region 28 and an unlined region 30, although in other designs the entire endoprosthesis 10 is lined and is characterized by an absence of an unlined region. In intrahepatic portosystemic shunt configurations, the graft-lined region 28 corresponds to an intrahepatic region and the unlined region 30 corresponds to a portal region. The graft-lined region 28 defines a first end portion 32, a middle portion 34, and a second end portion 36. The border between the graft-lined region 28 and the unlined region 30 is indicated by a circumferential radiopaque gold marker band 38 proximate, or just proximal to, the border. An additional radiopaque gold marker is optionally located on the proximal end 22 of the endoprosthesis 10.

The middle portion 34 of the graft-lined region 28, and in particular the portion of the endoprosthesis 10 corresponding to the controlled expansion element 20, forms a diametrically controlled portion of the endoprosthesis 10. As shown, the diametrically controlled portion of the endoprosthesis 10 (the middle portion 34 in FIG. 1), extends for less than an entire length of the endoprosthesis 10, and in particular less than a full length of the graft-lined region 28, although in other embodiments the controlled expansion extends for any desired length, including the full endoprosthesis length as desired.

As shown, the middle portion 34 corresponding to the controlled expansion portion of the endoprosthesis 10 has a first flared end 40, a central portion 42, and a flared second end 44. The first and second flared ends 40, 44 taper in different directions and at taper angle relative to the longitudinal axis of the endoprosthesis 10 (e.g., at a relative angle from about 10-80 degrees, including any value therebetween, such as about 60 degrees). Although the flared ends 40, 44 are shown with generally linear tapers, curved tapers, re-curved tapers, combined linear and curved tapers, and others are contemplated. The first and second flared ends 40, 44 help provide a smooth transition to the adjacent, first and second end portions 32, 36 when the endoprosthesis 10 is in an unconstrained state following initial deployment. Although the central portion 42 is shown as having a substantially uniform diameter, the central portion 42 optionally includes one or more tapers as desired, as can any of the other portions of the endoprosthesis 10.

The middle portion 34 of the graft-lined region 28 is constrained with the controlled expansion element 20 such that the endoprosthesis 10 exhibits an initial diametric expansion limit at the middle portion 34 to which the endoprosthesis 10 is deployed and which the endoprosthesis maintains prior to one or more subsequent mechanical adjustment steps. As shown in FIG. 1, the expansion element 20 causes the middle portion 34 to take on a dog-bone shape or hourglass shape, although any of a variety of shapes are contemplated. As shown in FIG. 1, the endoprosthesis 10 defines a minimum inner diameter (ID) at a boundary 46 between the central portion 42 and the first flared end 40.

The diameter of the endoprosthesis 10 in the middle portion 34 is smaller than the adjacent portions of the endoprosthesis 10 because the controlled expansion element 20 diametrically constrains self-expansion of the stent 12, but is able to be mechanically adjusted by a distensive force (e.g., using a balloon catheter) to allow diametric adjustment. To that end, if the controlled expansion element 20 was removed from the endoprosthesis 10 the stent 12 and base graft 18 would tend to self-expand to a maximum diametric expansion limit. In particular, the stent-graft 12, 18 is configured to expand to a maximum diameter (e.g., the manufactured diameter of the stent-graft) at which point further expansion is significantly resisted (e.g., resistance of 1000 ATM or more) and may even result in failure if an attempt to force the stent-graft 18 beyond that diameter is attempted. The stent 12, the graft 18, or the combination of the stent-graft 12, 18 can be configured to set this maximum diametric adjustment limit, beyond which the endoprosthesis 10 is not intended to be diametrically adjusted. In the same way, if balloon dilation is used to diametrically expand the controlled expansion element 20, middle portion 34 will expand correspondingly, up to a diameter of the adjacent, first and second end portions 32, 36 (e.g., as shown in FIG. 3) which represent the fully expanded diameter of the stent—graft 12, 18.

FIG. 3 shows the endoprosthesis 10 expanded to a maximum diametric expansion limit imparted by the remainder of the endoprosthesis 10, for example imparted by the base graft 18. As shown, the lined region 28 has a maximum diametric expansion limit corresponding to the base graft 18 having a continuous cylindrical profile through the first end portion 32, the middle portion 34, and the second end portion 36. As previously referenced, the stent-graft 12, 18 may have an "as manufactured" diameter, beyond which the stent-graft 12, 18 is not meant to expand in typical use, whether under physiological conditions or by balloon expansion.

In one example, the ID of the endoprosthesis 10 upon deployment at the middle portion 34 is approximately 8 mm and is expandable to approximately 10 mm. In some examples, the ID of the endoprosthesis 10 at the middle portion 34 (e.g., as measured at the minimum ID location 46) is expandable by 12% to 40%, for example. In still other embodiments, the endoprosthesis 10 at the middle portion 34 is expandable greater than 40%, such as up to 70% or even more.

For application in a TIPS procedure, the endoprosthesis 10 would typically have dimensions as follows: a length of about 5 to 12 cm, with a length of about 6 to 10 cm being more typical; a deployed diameter of about 5 to 14 mm, with a diameter of about 8 to 12 mm being more typical; and a total wall thickness of about 0.1 to 1.0 mm, with about 0.1 to 0.6 mm being more typical. While the dimension "diameter" is used herein, it should be understood that this dimension is intended to define an average cross-sectional dimension and is not intended to limit designs to circular cross-sectional shapes. Moreover, as shown in FIG. 1, the endoprosthesis 10 may be configured to exhibit multiple average cross-section dimensions along the length of the endoprosthesis 10, including tapers along different portions of the endoprosthesis 10.

In some embodiments, the endoprosthesis 10 itself has a compacted dimension suitable for endoluminal deployment, such as less than or equal to 16 French (5.3 mm), although a variety of dimensions are contemplated depending upon the treatment in which it is applied. In some embodiments, in order to be delivered percutaneously, the endoprosthesis 10 and its deployment apparatus have a diameter of less than about 13 French (4.3 mm), for example, although a variety of dimensions are contemplated. "French" measurements as used herein define the size of a hole through which a device will pass. For example, a device with a measurement of "10 French" will pass through a 10 French hole (which has a diameter of 3.3 mm). Again, the device need not have a circular cross-section in order to pass through a circular 10 French hole so long as the hole is large enough to accommodate the widest cross-sectional dimension of the endoprosthesis 10.

The first segment 14 of the endoprosthesis 10 will typically comprise about 50 to 90 percent of the entire length of the endoprosthesis 10. Accordingly, the first segment 14 will typically be about 4 to 8 cm in length and the second segment 16 will typically be about 1 to 3 cm in length, although a variety of dimensions are contemplated. The middle portion 34 of the graft lined region 28 corresponding to the controlled expansion element 20 typically has a total length of about 1 to 11.5 cm, where the first flared end 40 has a length of about 0.25 to 1.5 cm, more typically 0.5 cm, the central portion 42 has a length of about 0.5 to 8.5 cm, with 1.5 to 5.5 cm being more typical, and the flared second end 44 has a length of about 0.25 to 1.5 cm, with 0.5 cm being more typical, although a variety of dimensions are contemplated.

The stent 12 optionally includes any number of segments and configurations, according to various embodiments. As shown in FIG. 1, the first segment 14 has an undulating, helical stent pattern, although other configurations are contemplated. In turn, the second segment 16 optionally employs a different stent pattern from that of the first segment 14. For example, the second segment 16 is shown with an interlocked (or "chain-linked") stent pattern that helps prevent the second segment 16 from excessively longitudinally elongating beyond a predetermined desired length, although other configurations are contemplated. In some interlocked designs, a single wire is employed for the second segment 16, where the wire is wrapped from the cover 18 to a distal end 24 of the endoprosthesis 10 and then back to the cover 18 such that the wire terminates within the cover 18 and avoids having a loose end of the wire exposed at the distal end 24 of the endoprosthesis 10.

In some methods of forming the interlocked (or "chain-linked") stent pattern of the second segment 16 a single wire is wrapped from the first segment 14 to the distal end 24 of the endoprosthesis 10 and then back to the first segment 14. Along the length of the second segment 16 the wire is provided with a second undulated pattern along a first pass and a third undulating pattern, interlocking with the second undulating pattern along a second pass. By interlocking the second undulating pattern and the third undulating pattern, the stent pattern permits the second segment 16 to be longitudinally compressed, thus imparting flexibility; but the stent pattern prevents the second segment 16 from being longitudinally elongated beyond a predetermined maximum length. It should be noted that the interlocked stent pattern also imparts columnar support when the device is in a radially compressed configuration and less so when it is deployed. Examples of suitable stent patterns and associated methods of manufacture for the first and second segments are also described in U.S. Pat. No. 6,673,102 to Vonesh et al.

The first and second segments 14, 16 of the stent 12 may be formed from a variety of wire materials, including stainless steel, nickel-titanium alloy (nitinol), tantalum, elgiloy, various polymer materials, such as poly(ethylene terephthalate) (PET) or polytetrafluoroethylene (PTFE), or bioresorbable materials, such as levorotatory polylactic acid (L-PLA) or polyglycolic acid (PGA). In various examples, the stent 12 is self-expanding and exerts a self-expansion force on the endoprosthesis 10 when constrained. As such, in various designs the first and second segments 14, 16 of the stent 12 are formed of superelastic materials, such as nitinol metal, that will withstand tight compression in a compacted configuration (diameter) and then self-expand to a deployed configuration (diameter) once released in place, such as those described in U.S. Pat. No. 6,673,102 to Vonesh et al.

Although the endoprosthesis 10 is generally described as including a self-expanding stent 12, it should be understood that the stent 12 may include one or more balloon expandable portions (e.g., the second segment 16 may be balloon expandable) or the entire stent 12 may be balloon expandable with the endoprosthesis 10 being free of any self-expanding stent components. For example, the controlled expansion element 20 is optionally employed with a balloon expandable stent-graft and allows diametric adjustment beyond an initial deployment diameter through a plurality of adjusted diameters up to a maxim diametric expansion limit of the balloon expandable stent-graft.

In general terms, the cover 18 helps provide the endoprosthesis 10 with a flow lumen. In intrahepatic shunt applications, the cover 18 performs a number of functions in the endoprosthesis 10, including preventing extrusion of liver tissue through the stent 12, maintaining the maximum diametric dimensions of the endoprosthesis 10, preventing uncontrolled elongation of the stent 12, reducing or eliminating bile from permeating into the shunt, and facilitating bending without kinking, for example. As previously described, the controlled expansion element 20 optionally enhances or augments one or more functions of the base graft 18 beyond diametric adjustability. For example, the controlled expansion element 20 optionally provides enhanced impermeability performance, longitudinal strength, or others.

As shown in FIG. 2, the preferred material for the base graft 18 includes a base tube 48a, an inner film 48b, and an outer film 48c. The base tube 48a may be a fluoropolymer material and especially expanded polytetrafluoroethylene (PTFE). The inner film 48b is also optionally a fluoropolymer, and especially expanded PTFE. For example, the base tube 48a may be an extruded, thin-walled expanded PTFE base tube and the inner film 48b a plurality of layers of expanded PTFE film helically wrapped over the base tube. The outer film 48c is also optionally a fluoropolymer, such as a porous composite film of FEP and expanded PTFE. Examples of suitable materials for base tube 48a, inner film 48b, and outer film 48c are described in U.S. Pat. No. 6,673,102 to Vonesh et al. As shown, the base graft 18 is substantially continuous and uninterrupted in that the wall does not have any apertures or holes of sufficient size to remain patent in vivo, although grafts 18 with apertures or openings (not shown) configured to remain patent in vivo are also contemplated in other applications. The inner and/or outer film layers 48b, 48c optionally lend increased radial, or hoop strength to the base graft 18 and help to set the maximum diametric expansion limit of the stent-graft 12, 18 at the as manufactured diameter of the stent-graft 12, 18.

The stent 12 and the base graft 18 are secured together to provide a stent-graft 12, 18. For example, the first segment 14 is secured to the base graft 18 and an end of the second segment 16 is optionally secured to the base graft 18 and/or first segment 14. As shown, one or more layers of the base graft 18 is positioned interior of the stent 12 to define the inner lumen 26, although the base graft 18 is optionally positioned entirely outside of the stent element 12 or with the stent 12 embedded into the base graft 18, for example. As shown, a majority of the second segment 16 of the stent 12 is left uncovered, with an end of the second segment 16 secured to the base graft 18 (e.g., a single "row") and a remainder of the second segment 16 extending from the base graft 18. As shown, none of the interstices of the second segment 16 are covered such that fluid is able to flow through the interstices. In an intrahepatic shunt application, the second segment 16 is left uncovered to facilitate perfusion of portal venous branches via blood flow through the interstices of the second segment 16.

The base graft 18 is preferably attached to the stent 12 by bonding or otherwise attaching the two together through use of a suitable adhesive, such as fluorinated ethylene propylene (FEP), polyurethane, cyanoacrylates, or others. Additionally, the materials may be bonded or otherwise attached together through heat treatment (such as, sintering of the materials together) or through use of a wrap (for instance a tube, tape, or membrane) around the outside of the stent and cover (either continuous or discontinuous) that is adhered through either a thermoplastic or thermoset adhesive to the stent and cover. Alternatively, the stent 12 may also be coated with a thermopolymer or thermoset adhesive and the cover bonded or otherwise attached by reflowing or setting the polymer coating. In still other embodiments, the stent 12 and base graft 18 are mechanically attached (e.g., using sutures).

In some methods of making the endoprosthesis 10, the stent 12 is positioned as desired over a portion of the base graft 18 (e.g., over a base tube and layers of wrapped expanded PTFE) and a porous composite film of FEP and expanded PTFE is wrapped over the construction with the side of the film containing FEP toward the lumen of the base graft 18. The first segment 14 of the stent 12 is optionally coated with an adhesive, such as FEP, placed around the base tube 48a and inner film 48b, and is in turn covered by the outer film 48c. The assembly can then be heated at one or more points in the assembly process to bond or otherwise attach the various layers together as described in U.S. Pat. No. 6,673,102 to Vonesh et al.

In some embodiments, the controlled expansion element 20 is configured to be mechanically adjustable under pressure greater than typical biological pressures (e.g., typically circulatory pressures) and any expansion force exerted by the stent 12. For example, the controlled expansion element 20 is optionally mechanically adjustable by causing controlled expansion material forming one or more portions of the element 20 to yield or plastically deform, by causing reorganization of a fibrillary or other microstructure of such controlled expansion material, by release of fasteners or folds of the element 20, or other mechanical adjustment of the controlled expansion element 20. The pressure required to mechanically adjust the controlled expansion element 20 is greater than typical physiologic conditions (e.g., typical maximum blood pressures) such that the controlled expansion element 20 is able to maintain the adjusted diameter at less than a pressure that would tend to cause the stent-graft 12, 18 to catastrophically fail by exceeding the maximum diametric expansion limit of the stent-graft 12. The controlled expansion element 20 is preferably configured to maintain a diameter to which it is mechanically adjusted without substantial diameter creep or spontaneous diametric expansion over time under typical biological conditions. The controlled expansion element 20 optionally includes one or more layers and may be formed from a variety of materials, including fluoropolymer materials such as the distensible, expanded PTFE tube described in U.S. Pat. Nos. 3,953,556, 3,962,153, 4,096,227, 4,187,390, and 4,902,423, to Gore or the distensible lattices of U.S. 2013/0204347 to Armstrong, et al.

In some embodiments, the controlled expansion element 20 is formed of controlled expansion material including a bilayer compressed composite material formed of layers each including unsintered expanded PTFE and a stabilizing layer, such as a continuous layer of FEP. In some embodiments, the unsintered aspect of the expanded PTFE contributes to the expandability of the controlled expansion material. Unsintered expanded PTFE can be manufactured by extrusion followed by concurrent heating and stretching. Sintered expanded PTFE is manufactured by extrusion, concurrent heating and stretching, and sintering (heating to above the PTFE crystalline melting point temperature). Because unsintered expanded PTFE is heated to a lesser extent than sintered expanded PTFE, unsintered expanded PTFE material has greater conformability and greater stretchability than sintered expanded PTFE. The unsintered expanded PTFE has nonbent fibrils that can elongate approximately 40% or more before rupture, for example.

In some methods of manufacture, one or more wraps of the unsintered expanded PTFE/FEP composite material are overlapped to comprise the controlled expansion element 20. The FEP bonds together the multiple wraps of unsintered expanded PTFE to create a monolithic sleeve structure, for example, although a variety of configurations are contemplated (e.g., rings, collars, cylinder segments). For example, the controlled expansion element is optionally formed by cutting the unsintered and compressed, or densified, controlled expansion material into strips that are helically wound onto a cylindrical mandrel. One or more layers are formed in one or more passes to form a sleeve. In some embodiments, the material is wound so that the FEP side of the controlled expansion material faces outward. Any number of additional layers (e.g., an attachment or bonding layer) may also be applied over the controlled expansion element 20 as desired at any point in the process of forming the controlled expansion element 20 and/or during assembly of the endoprosthesis 10. The diameter of the cylindrical mandrel determines the initial inner diameter of the controlled expansion element 20.

In some methods, the controlled expansion element 20 is then heated, while still on the mandrel, to activate the FEP adhesive. The heat causes the FEP to flow, thereby creating a functionally unitary multi-layered sleeve of unsintered expanded PTFE. After cooling, the controlled expansion element 20 is removed from the mandrel and the ends of the controlled expansion element 20 are trimmed to create a sleeve of a desired length. The controlled expansion element 20 also optionally has a substantially continuous and uninterrupted wall characterized by the absence of apertures or holes configured to remain patent in vivo.

In some methods of assembly, the controlled expansion element 20 is placed onto an underlying portion of the endoprosthesis 10, such as the stent 12 and base graft 18 (collectively, "stent-graft 12, 18"), although a variety of configurations are contemplated, including the controlled expansion element 20 being secured inside of the stent-graft 12, 18. In some methods of assembly, the pre-assembled stent-graft 12, 18 is pulled through a loading funnel and into a tube with an outer diameter that is smaller than the inner diameter of the controlled expansion element 20. The tube containing the stent-graft 12, 18 is placed within the controlled expansion element 20 and the tube is removed from the stent-graft 12, 18. Upon emergence from the tube, the stent-graft 12, 18 self-expands to conform to the inner diameter of the controlled expansion element 20. As shown in FIG. 1, the controlled expansion element 20 has a length selected to be shorter than the base graft 18 such that a partial segment of the base graft 18 corresponding to the middle portion 34 is covered by the controlled expansion element 20.

In some embodiments, the controlled expansion element 20 is coupled to a portion of the remaining endoprosthesis 10 mechanically (e.g., by interference fit, friction fit, sutures, or others). In other embodiments, the controlled expansion element 20 is alternatively or additionally secured to the endoprostheses using a bonding agent (e.g., an adhesive such as FEP) between the endoprosthesis and the controlled expansion element 20. The bonding agent is optionally applied as a continuous layer or a discontinuous layer over substantially all the interface between the controlled expansion element 20 and the remaining endoprosthesis 10 or over only one or more portions of the interface between the controlled expansion element 20 and the remaining endoprosthesis 10. Though less desirable in controlled expansion elements 20 in which it is desirable for the material to remain unsintered, in some embodiments the controlled expansion element 20 is alternatively or additional coupled to the graft by a heating operation (e.g., by a global sintering or localized sintering at one or more selected portions of the interface between the controlled expansion element 20 and the remaining endoprosthesis 10).

In some embodiments, an inner diameter set process is performed for coupling the controlled expansion element 20 to the stent-graft 12, 18 prior to collapsing the endoprosthesis 10 into a delivery configuration. Some set processes include pulling the stent-graft 12, 18 with controlled expansion element 20 placed on it over a mandrel (not shown) having a larger outer diameter than the initial ID of the assembled endoprosthesis 10. The mandrel has an outer diameter (OD) corresponding to the shape of the middle portion 34 and the desired initial diametric expansion limit of the endoprosthesis 10 (the ID to which the endoprosthesis self-expands to in vivo following deployment prior to mechanically adjusting the controlled expansion element 20). For example, in an endoprosthesis adjustable between 8-10 mm, the controlled expansion element 20 would cause the endoprosthesis 10 to have an ID less than 8 mm and the OD of the mandrel would be 8 mm such that after the set process the controlled expansion element 20 is mechanically adjusted and the endoprosthesis 10 exhibits an 8 mm ID. In some embodiments, the mandrel has flared ends corresponding to the ends of the controlled expansion element 20 to provide flared ends to the controlled expansion element 20 and a smoother transition between the segment of the stent-graft 12, 18 constrained by the controlled expansion element 20 and adjacent segments of the stent graft 12, 18. Although the mandrel may have a continuous diameter between flared ends, any number of flares, tapers, curves, or other features are contemplated for imparting corresponding features to the portion of the endoprosthesis 10 corresponding to the controlled expansion element 20.

The set process causes the controlled expansion element 20 to conform to the outer surface of the endoprosthesis 10, which is believed to help hold the controlled expansion element 20 in place through subsequent processing, deployment, and implantation of the endoprosthesis 10 without the use of thermal and/or adhesive bonding. In some embodiments, the absence of thermal and/or adhesive bonding or other attachment along at least a portion of the interface between the controlled expansion element 20 and the stent-graft 12, 18 defines a sliding interface that helps allow the controlled expansion element 20 to slide on the surface of the stent-graft 12, 18 when ballooned, thus limiting the amount of foreshortening the controlled expansion element 20 translates to the stent-graft 12, 18. For example, an interference fit between the stent graft 12, 18 and controlled expansion element 20 provides a sliding interface between the components, according to some embodiments. In different terms, during diametric expansion of the endoprosthesis 10, the sliding interface between the controlled expansion element 20 and the stent-graft 12, 18 permits at least a portion of the controlled expansion element 20 to change in longitudinal dimension (e.g., contract during radial expansion) at a different rate than the stent-graft 12, 18 at the sliding interface.

In some other embodiments, a portion of the interface between the controlled expansion element 20 and stent-graft 12, 18 is adhesively bonded. For example, in some embodiments a fluoropolymer adhesive is used, such as tetrafluoroethylene (TFE) and perfluoromethyl vinyl ether (PMVE) described in U.S. Pat. No. 7,462,675 to Chang et al., FEP (fluorinated ethylene propylene), or PFA (perfluoroalkylvinyl ether/tetrafluoroethylene copolymer), for example. The adhesive is optionally applied on the inner diameter of the controlled expansion element 20, for example at each end of the controlled expansion element 20 but not at the central region, although a variety of configurations are contemplated. After the controlled expansion element 20 is placed on the stent-graft 12, 18 the adhesive is activated by applying heat thereto, for example without causing sintering, or at least without causing significant sintering, of the controlled expansion material 20.

Figures 4, 5:
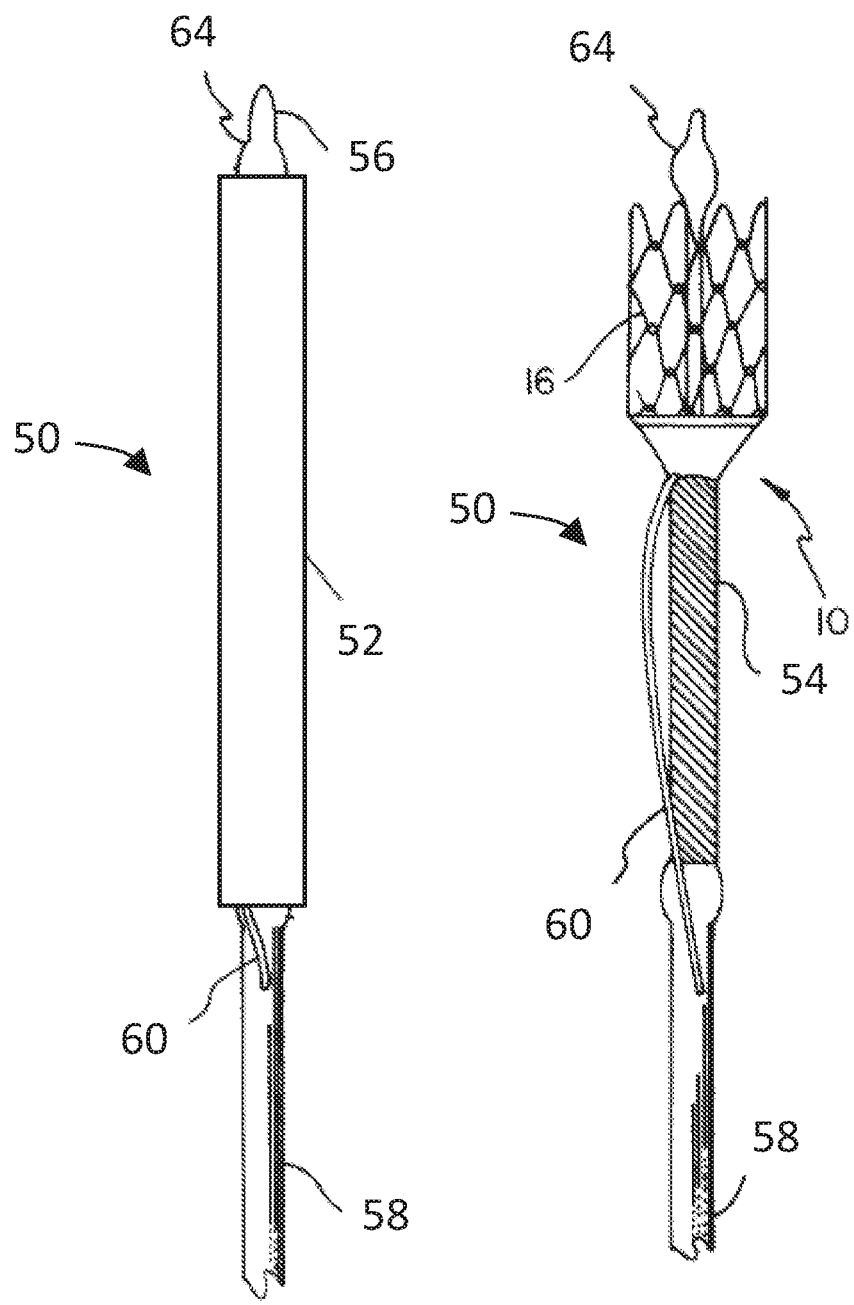
FIGS. 4 and 5 show a portion of a delivery system for use with the endoprosthesis of FIG. 1, according to some embodiments.

In still other embodiments, the controlled expansion element 20 is adhered along the entire interface or a majority of the interface the controlled expansion element 20 forms with the remaining endoprosthesis 10. For example, in some embodiments including a controlled expansion element having an outer layer of FEP, the controlled expansion element 20 is everted prior to applying it over the stent-graft 12, 18. The eversion of the controlled expansion element 20 repositions the FEP that was previously on the outer diameter (abluminal surface) of the controlled expansion element 20 to the inner diameter (luminal surface). FIGS. 4 and 5 illustrate a distal portion of a delivery system 50 for delivering and deploying the endoprosthesis 10 to a desired location for treatment, according to some embodiments. The delivery system 50 is a catheter-based, multi-staged deployment system including various features such as those described in U.S. Pat. No. 6,673,102 to Vonesh et al. As shown, the delivery system 50 includes an introducing (or packaging) constraint 52, a delivery constraint 54, a distal catheter shaft 56, and a proximal catheter shaft 58 (partially shown and extending proximally in FIGS. 4 and 5). FIGS. 4 and 5 also show a cut off view of a deployment line 60 attached to a delivery constraint 54 having a sufficient length to be externally manipulated to release the delivery constraint 54 from the endoprosthesis 10. During endovascular deployment, the delivery system 50 is passed through an introducing catheter (not shown) extending to a target location in the body of a patient.

In some embodiments, the introducing constraint 52 is a tube slidably received over the endoprosthesis and functions to maintain the second segment 16 of the stent 12 in a compacted, delivery profile. As described below, the introducing constraint 52 assists with transferring the endoprosthesis 10 into an outer catheter tube (e.g., an introducer) with the second segment 16 maintained in the compacted, delivery profile in the catheter tube (not shown).

For example, FIG. 4 corresponds to a state in which the endoprosthesis 10 is fully constrained at a delivery diametrical dimension and FIG. 5 shows the endoprosthesis 10 partially deployed, and in particular with the second segment 16 of the stent 12 allowed to deploy (e.g., via self-expansion). When the second segment 16 of the endoprosthesis 10 is unconstrained, the second segment 16 will expand to close to its fully deployed diameter. The remainder of the endoprosthesis 10, however, is contained within a delivery constraint 54 at a delivery diametrical dimension. In operation, the constrained endoprosthesis 10 will pass from the introducing constraint 52 into a catheter tube of approximately equal inner diameter (not shown) extending past the ultimate deployment site. Deployment of the second segment 16 will occur when the endoprosthesis 10 is extended from the catheter tube (not shown) at the deployment site (e.g., by retracting the catheter tube, extending the second segment 16 from the catheter tube, or a combination thereof).

The delivery constraint 54 maintains the first segment 14, base graft 18, and controlled expansion element 20 in a collapsed state at a delivery diametrical dimension. In some embodiments, the delivery constraint 54, also described as a constraining element, comprises a plurality of interwoven threads that are capable of being unwoven upon pulling the deployment line 60 at which point the delivery constraint 54 is deconstructed and pulled from the away from the endoprosthesis 10 through the delivery system 50. For example, the deployment line 60 extends through the proximal shaft 58 toward a proximal end of the system 50 where it can be manipulated externally to a patient by a user. Examples of knit, or interwoven delivery constraints are disclosed in U.S. Pat. No. 6,673,102 to Vonesh et al. and U.S. Pat. No. 6,224,627 to Armstrong et al. In other embodiments, the delivery constraint 54 is a sheet of material having two ends secured together that are able to be released upon actuation of a deployment line. In still other embodiments, the delivery constraint 54 is a distal end of a catheter sheath that is able to be actuated and removed from the stent-graft 12, 18 to permit self-expansion to the initial deployed state of the stent-graft 12, 18.

Figure 6:
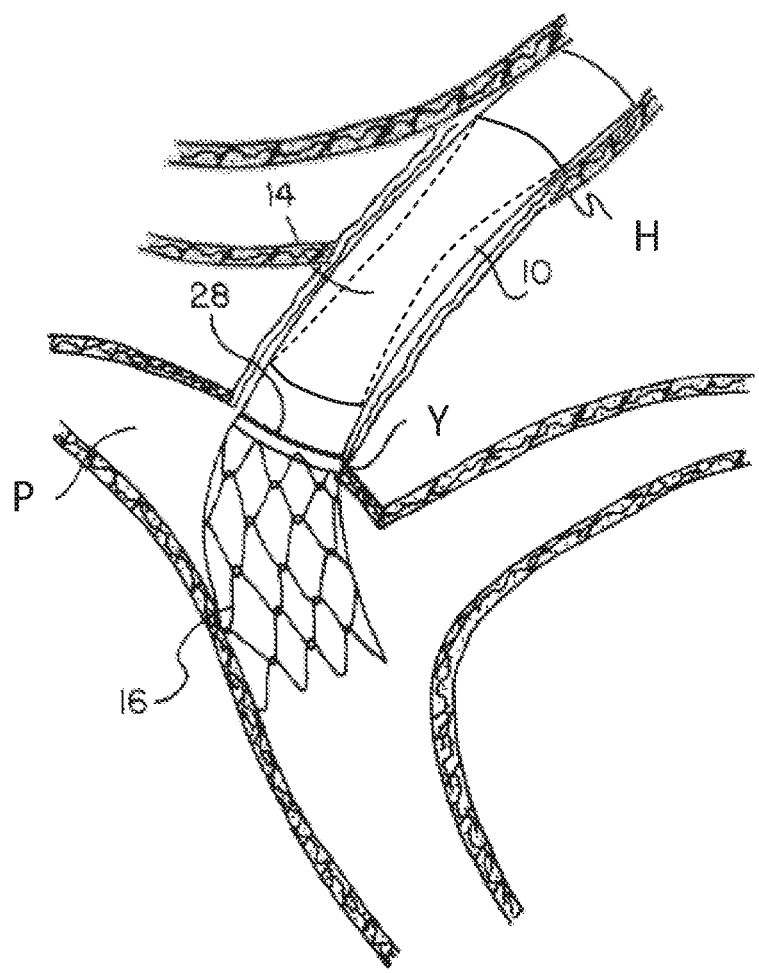
FIG. 6 shows the endoprosthesis of FIG. 1 deployed in a patient, according to some embodiments.

FIG. 6 shows the endoprosthesis deployed in an intrahepatic portosystemic shunt. Methods of operating the delivery system and deploying the endoprosthesis that follow are made with reference to FIGS. 4-6 in the contact of an intrahepatic shunt procedure, although a variety of applications are contemplated.

A catheter tube (not shown) is advanced into a portal vein P of a patient though a pathway formed through the liver from the haptic vein H to the portal vein P. A compacted endoprosthesis 10, mounted within the introducing constraint 52 is inserted into a proximal end of the catheter tube by manipulating the proximal shaft 58 to cause the second segment 16 to become transferred from the introducing constraint 52 into the catheter tube. The endoprosthesis 10 is then advanced through the catheter tube through the inferior vena cava, the hepatic vein H, the intrahepatic tract (shunt) formed in the liver, and well into the portal vein P. Radiopaque tip 64 can be aligned with the end of the catheter tube. Radiopaque markers associated with the endoprosthesis 10, such as the band 38 (FIG. 1) can be used to position the end of the base graft 18 adjacent to the intrahepatic juncture site Y such that the second segment 16 extends into the portal vein P. The catheter tube is withdrawn proximally, which permits the second segment 16 to fully expand within the portal vein P. The proximal catheter shaft 58 is then withdrawn through the catheter tube to seat the endoprosthesis 10 so that the unlined portal region is in the portal vein P of the liver and the graft-lined region 28 is engaged with the ostium of the tunnel in which the endoprosthesis 10 is being deployed, corresponding to the intrahepatic juncture Y. Alignment can be confirmed fluoroscopically by correct orientation of one or more radiopaque markers. In some embodiments, the endoprosthesis 10 is optionally deployed into the lumen of a previously deployed endoprosthesis (not shown) forming the shunt to augment or correct the performance of a previously deployed endoprosthesis, for example.

Once the endoprosthesis 10 is properly aligned, the delivery constraint 54 is removed by actuating deployment line 60, allowing the first segment 14 of the endoprosthesis 10 to enlarge in place in a tip-to-hub direction. As is illustrated in FIG. 6, the deployment procedure aligns the covered portion of the endoprosthesis 10 within the intrahepatic tract (shunt). Further, the uncovered second segment 16 permits blood flow both to enter the endoprosthesis 10 and to continue through the portal vein P. The result is that excess pressure can be relieved from the portal system (through the shunt formed by the endoprosthesis 10) without completely eliminating normal blood flow through portal vein P. The broken lines in FIG. 6 illustrate the endoprosthesis expanded to the initial diametric expansion limit pre-set into the controlled expansion element 20. If desired, touch-up of the endoprosthesis 10 can be performed by subsequent balloon dilation of the endoprosthesis 10 at balloon diameters below those required to mechanically adjust the controlled expansion element 20 to an adjusted diameter.

Figure 7:
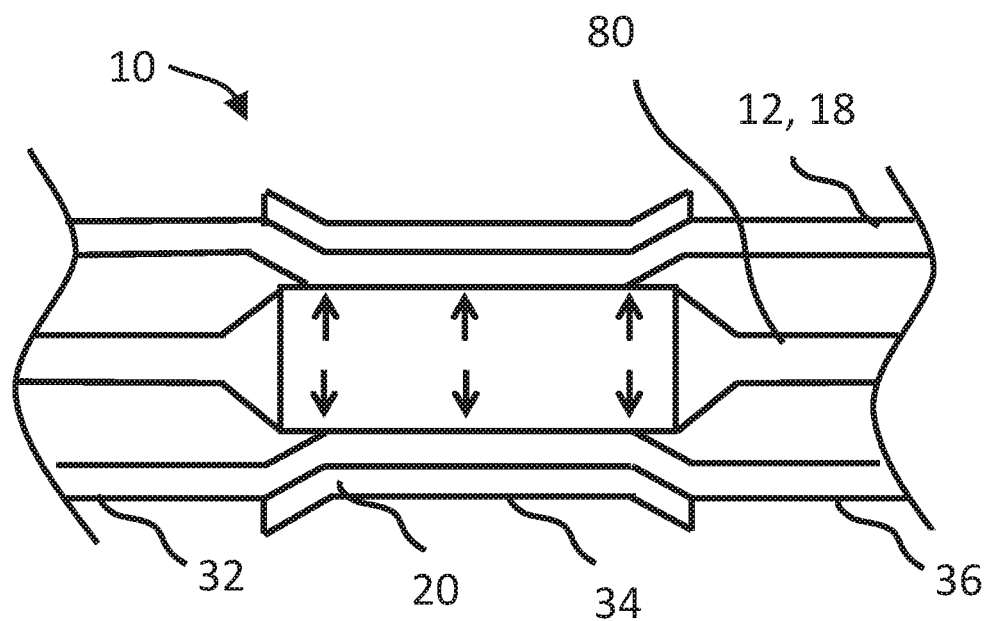
FIG. 7 shows a schematic representation of a balloon expansion of the endoprosthesis, according to some embodiments.

Some methods of forming an intrahepatic portosystemic shunt include positioning the endoprosthesis 10 in the liver of the patient at a delivery diametrical dimension. The endoprosthesis 10 is fully deployed such that the endoprosthesis self-expands in situ and is fully seated in the liver of the patient to form the intrahepatic portosystemic shunt, where the controlled expansion element 20 limits expansion of a partial segment of the stent-graft 12, 18 to an initial deployed diametrical dimension as shown in FIG. 6. This limited expansion restricts fluid flow through the shunt and impacts the pressure gradient between the portal vein P and the systemic venous circulation. The first end portion 32 (FIG. 1) and a second end portion 36 (FIG. 1) help anchor and seal the endoprosthesis 10 against the anatomy and prevent migration of the endoprosthesis 10. If a user (e.g., a clinician) wishes to increase the fluid flow to adjust the pressure gradient, the user can apply a distending force on controlled expansion element 20, for example by using a balloon catheter 80 (FIG. 7), to mechanically adjust the controlled expansion element 20 a desired amount (e.g., up to the maximum diametric expansion limit of the base graft 18, which is represented in solid lines in FIG. 6).

Figure 8:
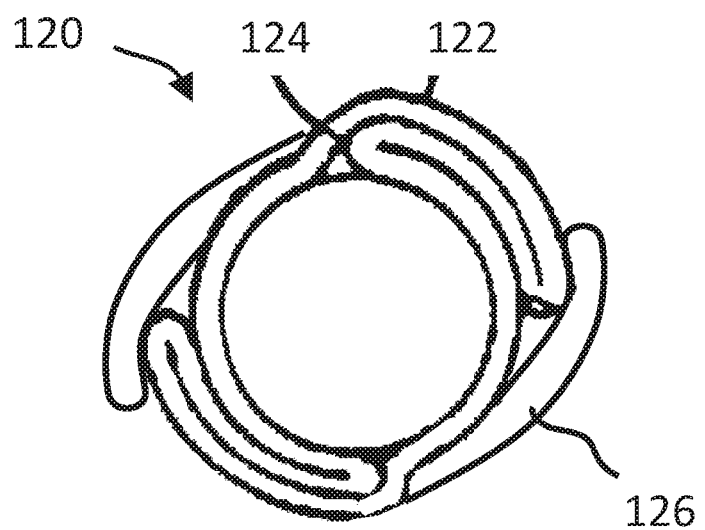
FIG. 8 shows a controlled expansion element, according to some embodiments.

FIG. 8 is a schematic illustration of dilation of a portion of the endoprosthesis 10 using the balloon catheter 80. In the schematic illustration, the stent 12 and base graft 18 are indicated collectively as a layer. As generally indicated, the entire middle portion 34 which corresponds to the controlled expansion portion of the endoprosthesis 10 need not be dilated or otherwise diametrically adjusted in a single step (e.g., where balloon length is less than the middle portion 34).

The diameter of the segment of stent-graft 12, 18 corresponding to the controlled expansion element 20 is able to be adjusted to any diameter between the initial delivery expansion limit and the maximum expansion limit by selection of maximum balloon diameter and/or balloon pressure. In other words, the diameter (e.g., including the minimum inner diameter (ID) at the location 46) is able to be selectively enlarged to an enlarged diametrical dimension, also described as an enlarged or adjusted diameter. The controlled expansion element 20 maintains the endoprosthesis 10 at the enlarged diametrical dimension and does not permit creep of the ID under typical physiologic conditions. Thus, the controlled expansion element 20 helps the endoprosthesis 10 maintain the enlarged diametrical dimension to permit increased fluid flow through the shunt (e.g., up to the maximum diametric expansion limit of the base graft 18, which then limits any further expansion).

Various methods of treatment include taking one or more pressure measurements and adjusting the endoprosthesis 10 according. For example, in an intrahepatic shunt procedure, portal hypertension may be assessed and treated using one or more of such pressure measurements and adjustments. Portal hypertension is an increase in the blood pressure within the portal venous system. Wedged hepatic venous pressure (WHVP), is used to estimate the portal venous pressure by reflecting not the actual hepatic portal vein pressure but the hepatic sinusoidal pressure. The hepatic venous pressure gradient (HVPG) is a clinical measurement of the pressure gradient between the WHVP and the free hepatic venous pressures, and thus is an estimate of the pressure gradient between the portal vein and the inferior vena cava.

In some embodiments, a user takes at least one pressure measurement after fully deploying the endoprosthesis to determine the pressure gradient between the portal vein and the systemic venous circulation, determines that adjustment is needed, and adjusts the diameter of the partial segment of the base graft 18 corresponding to the controlled expansion element 20. Any number of subsequent pressure measurements and enlarging adjustments are contemplated as part of a single procedure or multiple procedures. For example, in some treatment methods at least 24 hours pass between one or more pressure measurements and/or adjustments of the endoprosthesis 10, or an even greater amount of time. For example, it is contemplated that a diametric adjustment may occur as a separate procedure from the initial delivery procedure and formation of the shunt or as a separate adjustment procedure subsequent to a prior diametric adjustment procedure (e.g., performed at a later day, month, or even year).

In addition to, or as an alternative to being formed of controlled expansion material, the controlled expansion element 20 optionally includes one or more physical features, such as pleats, folds, or creases (FIG. 8) that are selectively secured in a closed configuration (e.g., by a bonding agent or material) and which can later be opened or separated by application of a distending force, thereby allowing the features to expand to mechanically adjust the diameter of the controlled expansion element 20. For example FIG. 9 shows a controlled expansion element 120 usable with any of the various features described above in association with endoprosthesis 10. The controlled expansion element 120 is generally sleeve-like, or cylindrical in configuration, is mechanically adjustable at distending forces greater than typical physiologic conditions (e.g., blood pressure), and can correspond to the diametrically controlled portion of the endoprosthesis 10, which is not shown in FIG. 8. As indicated in FIG. 8, the controlled expansion element 120 includes one or more layers forming a sleeve 122 that defines one or more expansion features 124 in the form of longitudinal pleats or folds. One or more securing elements 126, for example a tape material, such as ePTFE coated with FEP, secures the expansion features 124 in a closed state. Upon application of a distending force (e.g., balloon dilation), the securing elements 126 allow the expansion features 124 to expand (e.g., they plastically deform, break, or release) resulting in diametric adjustment of the diametrically controlled portion of the endoprosthesis 10.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. A method for treating portal hypertension, the method comprising:
    providing an endoprosthesis including a stent, a first graft portion, and a second graft portion extending along at least a portion of the first graft portion, the endoprosthesis being constrained to a first diametrical dimension by a delivery constraint for insertion into a lumen and configured to self-expand to a second enlarged diametrical dimension when the delivery constraint is released, the second graft portion defining a diametrically controlled portion of the endoprosthesis that is restricted from further diametrical enlargement by self-expansion to a restricted diameter;
    positioning the endoprosthesis in the portal vein and the hepatic vein;
    deploying the endoprosthesis to the second enlarged diametrical dimension by releasing the delivery constraint and allowing the endoprosthesis to self-expand, the diametrically controlled portion maintaining the restricted diameter under physiologic conditions so that the endoprosthesis has a first end having a first inner diameter and a second end having a second inner diameter, wherein the diametrically controlled portion is disposed therebetween and has a third inner diameter that is smaller than each of the first inner diameter and the second inner diameter; and
    performing a diametric adjustment of the endoprosthesis in situ, including diametrically expanding at least a portion of the diametrically controlled portion of the endoprosthesis to an adjusted diameter by applying distending force to the diametrically controlled portion of the endoprosthesis, the diametrically controlled portion of the endoprosthesis maintaining the adjusted diameter under physiologic conditions, wherein diametrically expanding the diametrically controlled portion of the endoprosthesis reduces a pressure gradient between the portal vein and the systemic venous circulation, the pressure gradient determined by taking a first pressure measurement near the first end of the endoprosthesis and a second pressure measurement near the second end of the endoprosthesis.

2. The method of claim 1, wherein diametrically expanding the diametrically controlled portion of the endoprosthesis deforms the second graft portion.

3. The method of claim 1, further comprising taking at least one pressure measurement, and then further diametrically expanding the diametrically controlled portion of the endoprosthesis to a second, enlarged diameter.

4. The method of claim 1, further comprising diametrically expanding the diametrically controlled portion of the endoprosthesis to a further enlarged diameter greater than the adjusted diameter.

5. The method of claim 1, further comprising diametrically expanding the diametrically controlled portion of the endoprosthesis to a maximum diametric expansion limit defined by the stent and the first graft portion.

6. The method of claim 1, further comprising performing a plurality of diametric adjustments of the endoprosthesis in situ.

7. The method of claim 1, wherein the endoprosthesis includes an unlined region, the method further comprising positioning the unlined region in the portal vein.

8. A method for treating portal hypertension, comprising:
providing an endoprosthesis including a stent, a first graft portion, and a second graft portion extending along at least a portion of the first graft portion, the endoprosthesis being constrained to a first diametrical dimension by a delivery constraint for insertion into a lumen and configured to self-expand to a second enlarged diametrical dimension when the delivery constraint is released, the second graft portion defining a diametrically controlled portion of the endoprosthesis that is restricted from further diametrical enlargement by self-expansion to a restricted diameter;
positioning the endoprosthesis in the portal vein and the hepatic vein;
deploying the endoprosthesis to the second enlarged diametrical dimension by releasing the delivery constraint and allowing the endoprosthesis to self-expand to form a shunt, the diametrically controlled portion maintaining the restricted diameter under physiologic conditions; and
taking at least one pressure measurement to determine a pressure gradient resulting from the shunt formed by the endoprosthesis between the portal vein and the systemic venous circulation at least 24 hours after formation of the shunt, wherein taking at least one pressure measurement includes measuring pressure near a first end of the endoprosthesis and measuring pressure near a second end of the endoprosthesis; and
diametrically expanding at least a portion of the diametrically controlled portion of the endoprosthesis by mechanically adjusting said portion of the diametrically controlled portion with a distensive force such that said portion of the diametrically controlled portion is enlarged and maintained at an enlarged diameter by the second graft portion to reduce the pressure gradient.

9. The method of claim 8, further comprising taking at least one pressure measurement after diametrically expanding said portion of the diametrically controlled portion of the endoprosthesis, and then further diametrically expanding said portion of the diametrically controlled portion such that at least a second portion of said portion of the diametrically controlled portion being maintained at the enlarged diameter by the second graft portion is further enlarged and maintained at a further enlarged diameter by the second graft portion to reduce the pressure gradient.

* * * * *